United States Patent [19]

Kontos et al.

[11] Patent Number: 5,525,352
[45] Date of Patent: Jun. 11, 1996

[54] CONFECTIONERY DELIVERY SYSTEM FOR PHARMACEUTICALLY ACTIVE SUBSTANCES

[76] Inventors: Angelos Kontos; Georgios C. Kontos, both of 4 Kerkyras Street, GR-146 71 Kastri, Greece

[21] Appl. No.: 244,817
[22] PCT Filed: Oct. 18, 1993
[86] PCT No.: PCT/GR93/00018
§ 371 Date: Jun. 28, 1994
§ 102(e) Date: Jun. 28, 1994
[87] PCT Pub. No.: WO94/09758
PCT Pub. Date: May 11, 1994

[30] Foreign Application Priority Data

Nov. 5, 1992 [GR] Greece ............... 920100490

[51] Int. Cl.⁶ ...................... A61K 9/20
[52] U.S. Cl. ...................... 424/440; 424/486
[58] Field of Search ................ 424/440, 441, 424/457, 468, 490; 426/101, 103, 66–68, 139, 312, 303, 565, 654, 558, 524, 660–662

[56] References Cited

U.S. PATENT DOCUMENTS

| | | | |
|---|---|---|---|
| 4,086,370 | 4/1978 | Olds et al. | 426/101 |
| 4,104,405 | 8/1978 | Forkner | 426/101 |
| 4,104,411 | 8/1978 | Poaler | 426/100 |
| 4,127,679 | 11/1978 | Amano et al. | 426/565 |
| 4,725,445 | 2/1988 | Ferrero | 426/565 |
| 4,749,575 | 6/1988 | Rotman | 424/441 |
| 4,785,833 | 11/1988 | Holzner et al. | 131/310 |
| 4,853,246 | 8/1989 | Stevens | 426/580 |
| 4,999,185 | 3/1991 | Takemori et al. | 424/441 |
| 5,135,767 | 8/1992 | Daouse | 426/515 |
| 5,343,710 | 9/1994 | Cathenaut et al. | 426/100 |

OTHER PUBLICATIONS

Derwent Publications Ltd., London, GB; AN 90-262116, Database WPI, Week 9035, & DK, A, 8 903 113 (Novo-Nordisk A/S) 13 Jun. 1990.
Derwent Publications Ltd., London, GB; AN 90-035088, Database WPI, Week 9005 & SE, A, 8 800 634 (Semper AB) 25 Aug. 1989.
Derwent Publications Ltd., London, GB; AN 85-185973, Database WPI, Week 8531, & JP, A, 60 112 720 (Kosaka) 19 Jun. 1985.
Derwent Publications Ltd., London, GB; AN 90-120673, Database WPI, Week 9016, & JP, A, 2 072 121 (Yakult Honsha KK et al.) 12 Mar. 1990.

*Primary Examiner*—Thurman K. Page
*Attorney, Agent, or Firm*—Ladas & Parry

[57] ABSTRACT

The invention relates to a confectionery form of matrix suited to contain microcapsules for controlled release of pharmaceutically active substances, of fixed content, which is soluble in the mouth and readily swallowed without chewing, as well as the process for the preparation thereof. In a preferred embodiment, the confectionery matrix is ice cream and a confectionery formulation is prepared by mixing he microcapsules with the ice cream in a liquid phase and then solidifying the mixture. The microcapsules are coated with a water-proof substance to protect the pharmaceutically active substances from eutectic water.

22 Claims, No Drawings

CONFECTIONERY DELIVERY SYSTEM FOR PHARMACEUTICALLY ACTIVE SUBSTANCES

The aim of the present invention is to propose a confectionery form of matrix suited to contain microcapsules for controlled release of pharmacologically active substances, of fixed content, which is soluble in the mouth and readily swallowed without chewing, as well as the process for the preparation thereof.

Since the microcapsules for controlled release of pharmacologically active substances are not resistant to the high pressures created in the tabletting machines, tablets containing microcapsules for controlled release of pharmaceutically active substances are rarely manufactured.

Thus, the most widespread form for the oral administration of microcapsules for controlled release of pharmaceutically active substances are the gelatin capsules.

However, many patients and particularly children refuse to swallow a medicine in the form of a usual gelatin capsule available in the market.

In these patients, the feeling that the capsule is a foreign body that may make them choke neutralizes the mechanism of swallowing.

The need consequently exists for the creation of a system of a matrix that would permit the easy oral administration of microcapsules for controlled release of pharmaceutically active substances, which is soluble in the mouth without chewing.

PRIOR STATE-OF-THE-ART

DE-A 336 216 describes a process for coating pharmaceutically active substances for the formation of microcapsules which are resitant to the pressures created during tabletting, nevertheless, it imposes considerable limitations in the selection of materials used for said coating.

FR-A 2011960 renders formulated pieces which include microcapsules containing pharmaceutically active substances administered orally, nevertheless, it presents the disadvantage that the mixture to be formulated is exposed to relatively high temperatures for considerable time, a fact which creates serious risks for alteration or for shortening of the shelf-life of various thermolabile pharmaceutical substances.

Patent Application EP-0 239983 describes a process which avoids the high temperatures employed in FR-A 2011960 but which, despite the fact that it makes use of readily melted mixtures, likewise strains, from the thermal point of view, even though to a smaller extent, the pharmaceutically active substances.

Patent Application EP-0 227603 grants a confectionery system for the administration of medicines by means of chewing but likewise strains, from the thermal point of view, the protected pharmaceutically active substances.

EP-A 0267160 describes a product which is likewise thermically strained in the course of its processing.

DESCRIPTION OF THE INVENTION

In accordance with the present invention, the aforementioned problem is solved by addition of the aforementioned known per se microcapsules for controlled release of pharmaceutically active substances (see for instance 1) Remington's Pharmaceutical Sciences Handbook, Mack, Publ. Co. New York U.S.A. 18th Edition Pages 1663–1665

2) M. Riag, N. Weiner, F. Martin in H. Lieberman, N. Prueger, G. Banker Eds.: Pharmaceutical Dosage Forms—Disperse Systems, Vol. 2

3) Jones D. M., Factors for consideration in fluid bed processing. *Pharmaceutical Technology*, April 1985

4) Ebert W. R., Pharm. Tech. I (10): 44, 1977

5) Madan P. L., Pharm. Tech. I (10): 68, 1978

6) Jager K. F. et al. "Effort of Material Motion on Agglomeration in the Rotary Fluidized-Bed Granulator" Drug Made in Germany, Vol. XXV pp. 61–65 (1982), incorporated to the present description by reference)

into a suitable low viscosity, fluid confectionery cream system of ice cream substitute under stirring, at a temperature ranging between $-1°$ C. and $0°$ C., and its immediate feeding into a device of continuous or non-continuous operation, for production and kneading of ice cream, where it is solidified, under nitrogen bubbling, under pressure, in a matrix for enclosure of microcapsules and it is formulated, preferably, in cup-shaped pieces or in ice cream borne on a small wooden rod, in certain cases of bulky pharmaceuticals, such as for instance in the case of cathartic plant fibers or of nutritive elements, which are administered in large single doses of up to approximately 100 grams, or in the shape of chocolate bars with subdivisions, bonbons, caramels, spheres, sugared pills, cylinders, olives, and in any kind of geometrical or artistic shape, or color, confectionery preparations of this sort, of low weight and of small dimensions, for all medicinal products that are usually administered each time in quantities below one gram, at a final temperature of $-18°$ C. It is evident to those skilled in the art that, when, in certain cases, it is necessary to effect an even better homogenizing of the microcapsules within the confectionery matrix, the formulated product may be recycled to the kneading department of the facility and subjected, once again, to the production process.

Futhermore, it is obvious that provision may be made, in the facilities for production and kneading of the ice cream, to have the scrapers of the cooling surfaces shorter and bearing soft elastic extremities on their edges, in order to avoid the creation of high pressures between the metal surface, which could eventually bring about the destruction of the coatings of the microcapsules. Of course, during the blowing of the nitrogen, the maintenance of the highest possible temperatures ensures, in the best possible manner, the protection of the coatings of the microcapsules.

Nevertheless, even at the temperature of $-18°$ C., there still exists, within the solid confectionery matrix that is so formed, a small quantity of water (A. W. Farall, Engineering for Dairy and Food Products, page 300) which contains dissolved amounts of sugar, glucose, milk salts, etc. and which has not solidified. In the long run, this constitutes a risk in keeping intact the totality of the microcapsules containing the active substance of the cathartic plant fibers etc.

The inventors have also solved the aforementioned problem in the following manner. The capsules and the water soluble plant fibers are rendered provisionally water-proof, at low temperatures below zero, before their addition to the binding confectionery mixture which creates the matrix that consists of the principle solid phase of the ice cream, the possibly minimal aforementioned eutectic still liquid phase and the abundant gaseous phase of the enclosed nitrogen. The provisional water-proofing is carried out inside a rotating, inclined with respect to the vertical axis, special container designed for the coating of tablets or microcapsules (coating-drum), by coating with an adequate amount of edible vegetal oil, such as for instances peanut oil, sesame oil, olive oil, palm oil, etc., which is added at a very slow rate in small doses, in the form of spray produced under very large pressure, and subsequently by blowing cool air at a temperature sufficiently lower than that of the melting point of the corresponding oil, in order to obtain the polishing of the microcapsules (microspherules). The coated microcapsules are transferred immediately to the stock container, under stirring, and are added to the aforementioned cream mixture which is likewise at a temperature of approximately 0° C. to −1° C. It would be clear to those of skill in the art that the water-proof microcapsules, instead of being added in the stirred stock container of the cream of the ice cream substitute, in their totality and in a precisely fixed ratio, may be fed into a special capsule-filling machine and dispensed with dosimetric accuracy into the corresponding forming molds of the aforementioned geometrically shaped formulations between two or more superposed layers of ice-cream substitute in the form of a sandwich. Alternatively, it may be possible to use, for the polishing process, anhydrous molten cooking milk butter, working under the same conditions of cooling.

If so desired, the microcapsules may be polished prior to the aforementioned provisional water-proofing by means of a mixture of synthetic waxes, on condition that the melting point of the latter is below 30° C. It is understood that other, known clear to those of skill in the art pharmacologically accepted hydrophobic substances may also be employed for the aforementioned provisional water-proofing, at low temperatures below zero, of the confectionery matrix enclosing the microcapsules, on condition that said substances melt instantaneously at the temperature of the mouth, such as for instance liquid paraffin or mixtures thereof. The quantity of wax employed is controlled by those of skill in the art so that, in association with the amount of solidified vegetal oil, it ensures the better water-proofing of the microcapsules (spherules) containing the pharmaceutically active substance.

The weight of the vegetal oils or butter and waxes used for the water-proofing of the microcapsules ranges between 0.5% and 20% of the weight of the microencapsulated pharmaceutically active substances and preferably between 7% and 18%.

The content of the microcapsules within the confectionery matrix ranges between 0.1% and 60%, preferably between 6% and 30%, and most preferably between 8% and 20% by weight. The limits within which the contents of the various components of the aforementioned matrix of confectionery composition, which is, as far as its taste is concerned, an ice cream substitute richer or poorer in calories, may vary, are indicated below.

| | |
|---|---|
| Water-proof microcapsules of pharmaceutically active substance | 0.1–25% |
| milk powder FAO/WHO | 1–18% |
| sugar USP | 10–18% |
| lecithin USP | 2–4% |
| casein USP | 0.5–4% |
| vegetal gum USP | 0.1–1% |
| synthetic sweetener USP | adequate amount |
| flavor USP | adequate amount |
| colorant USP | adequate amount |
| water USP, sufficient quantity up to | 100%. |

Without excluding the normal usage of air for the swelling (overrun) of the aforementioned ice cream substitute, the use of nitrogen or of any other inert gas is considered preferable for the better maintenance of the matrix.

In the present description, the percentage of swelling (overrun) of the ice cream is determined by the following quotient:

liters of final volume of ice cream—liters of initial mixture×100
liters of initial mixture The aforementioned nitrogen is introduced into the mass of the solidified and kneaded ice cream under pressure of up to 5 atmospheres from a nitrogen steel container.

The swelling (overrun) of the liquid initial confectionery mixture used may range from 30% up to 200% (volume/volume), preferably from 50% up to 150%, and is most preferably checked at 100% (volume/volume) which gives a smoother texture, in the mouth, to the cream of the ice cream which, at the temperature of the mouth, following a short stay therein, melts without having to be chewed.

The aforementioned formulated pieces may eventually be coated with one of the usual coatings such as chocolate, sugar, wafer or other from the confectionery point of view acceptable material or combination of materials, and may also bear subdividing scores. The aforementioned coating is carried out in accordance with the well known technology in the manufacture of ice cream, chocolate and caramels, in well known per se automatic machines (see for example:

1) Arthur W. Farall, Engineering for Dairy and Food Products, John Wiley and Sons Inc. pages 297–332, New York and London
2) Chocolate, Cocoa and Confectionery: Science and Technology, 2nd Edition, AVI Publishing Co. Inc., Westport, Conn. (1950)
3) Ice cream, 4th Edition (1986) AVI Publishing Co. Inc., which are incorporated herein by reference).

Prior to the application of the coating, the finished product that has been formulated in the proper matrix is frozen eventually below its storage temperature of approximately −20° C., at temperatures of −30° C. up to even −60° C., in order to enable even the outer surface of the ice cream that will come in contact with the possibly slightly warmer sugar-syrup of chocolate-syrup not to be subjected to any thermal strain whatsoever, not even instantaneous.

The abolition of the need for chewing brought about by this system for administration of pharmaceutically active substances eliminates the risk for application of great pressure, by the teeth, on the coatings of the active substances, which cause damage to said coatings and undesirable early release of the active substances into the mouth as well as the sense of unpleasant taste. Furthermore, it is known, from the principles of physical chemistry, that a storage temperature of the preparation of the present invention, which is 40° C. up to 80° C. lower than that of the ambient temperature, slows down by a multiple of $10^4$ up to $10^8$ approximately the rate of the reactions leading to the oxidation and the aging of the product. Furthermore, the enclosure of 100% up to 200%, by volume, of nitrogen in the preparation, in association with the flavorable influence of the low temperature on the suspension of all chemical, physicochemical or microbial alteration processes, significantly lengthens the shelf life of the preparation. Besides, in acocordance with Vant' Hoff's Law, a reduction of 10° C. in the temperature doubles or triples the preservation properties. It is obvious that, apart from the ice-cream composition proposed above, any composition of commercial ice-cream or ice-lolly may likewise be used for the purpose of the present invention.

The aforementioned formulated pieces may also be formulated within receptors made of composite sheet with layers of paper, plastic and/or metal, and be closed hermetically. In accordance with the well known pharmacotechnical practice for manufacture of dosage forms, the dimensions and the weight of the various formulations indicated above are determined in such a manner that, depending on the nature and on the content of the pharmaceutically active substance contained therein, said formulations are administered once up to three times daily to cover the needs of an adult patient of body weight 70 Kg.

Pharmaceutically active substances in the form of waterproof microcapsules for controlled release, which may be used in the present invention In the present description, the term microcapsules for controlled release of pharmaceutically active substances includes, apart from the totality of the capsules of enteric or gastric release which are known in the art, also the microcapsules whose only aim is the simple masking of the taste of the pharmaceutically active substance which they encapsulate until the latter pass through the mouth.

Furthermore, in the present description, the term microspherules and microcapsules is used indiscriminately and alternatively for practicles of dimensions ranging from a few tenths of a micrometer up to 5000 micrometers, preferably up to 1000 micrometers and more preferably up to 500 micrometers. Moreover, the term artistic shape includes all forms that are an artistic model of, for instance, a fruit or an animal or an object, etc., such as for example children's toys.

Only few of the numerous classes of pharmaceutical products that may be converted into microcapsules for controlled release and used for the production of confectionery preparations, in accordance with the present invention, are listed below:

1. Anti-inflammatory substances
2. Factors for dilatation of the coronary artery
3. Tranquillizers
4. Nutrient additives
5. Diuretics
6. Pharmaceuticals against migraine
7. Pharmaceuticals against angina pectoris
8. Expectorants
9. Antipyretics
10. Anti-cholesterinemic and anti-lipidemic agents
11. Anti-arrhythmics
12. Ion-exchange resins
13. Inorganic supplements such as potassium chloride, calcium carbonate, magnesium oxide and other salts of alkaline metals and of alkaline-earth metals
14. Laxatives
15. Vitamins
16. Compounds for the binding of the acids of the stomach
17. Antitussives
18. Antihistaminics
19. Various alkaloids
20. Decongestives As well as mixtures of microcapsules including chemically interacting incompatible with one another pharmaceuticals such as vitamin C and calcium carbonate or cholestyramine and potassium chloride.

For the better understanding of the present invention, two examples of its execution are given below, which, however, do not limit its scope.

EXAMPLE 1

| Composition of an ice-cream substitute | |
| --- | --- |
| Water-proof microcapsules of pharmaceutically active substance | 1000 g |
| Milk powder FAO/WHO | 470 g |
| Sacharose USP | 1500 g |
| Lecithin USP | 180 g |
| Casein USP | 50 g |
| Glucose USP | 180 g |
| Vegetal gum USP | 10 g |
| Synthetic sweetener USP | adequate amount |
| Flavor USP | adequate amount |
| Colorant USP | adequate amount |
| Water USP sufficient quantity up to | 10000 g |

Following complete dissolution of all the above mentioned excipients under stirring and eventual slight warming, they are transferred to the special continuous=operation machine for production of ice cream, in the cream feeding vessel.

The mixture is cooled to a temperature slightly below zero, and, under vigorous stirring, the pharmaceutically active substance is added all at once, starting at the same time the production of the ice cream and its swelling by 100% by means of nitrogen blown from a steel container. The above product is filled into recipients made of composite sheet and the formulated pieces are kept at a temperature of −40° C. with excellent results as regards their preservation.

EXAMPLE 2

| Composition of commercial ice-cream | |
| --- | --- |
| Water-proof microcapsules of pharmaceutically active substance | 1.5 Kg |
| Fresh milk | 6.4 Kg |
| Saccharose | 1.6 Kg |
| Milk cream | 1.6 Kg |
| Egg yolks | 0.3 Kg |
| Glucose | 0.15 Kg |
| Alpigen Super | 0.05 Kg |
| Couantreau | 0.03 Kg |
| half a teaspoonful of vanilla | |

Proceed as in case of example 1, with the only difference that the formulated pieces of ice cream are of the well known shape and dimensions of ice cream coated with chocolate that is held by means of a small wooden rod, or of ice-cream that is filled in cups of different sizes.

Note:

In working in accordance with the process indicated in example 1, for the same amount of microcapsules, we used, instead of the aforementioned synthesis of commercial ice-cream, a synthesis of commercial ice-lolly made of fruit juices, with equally satisfactory results.

We claim:

1. A process for preparation of a confectionery formulation for controlled release of a pharmaceutically active substance, said process comprising:

a) mixing a plurality of coated microcapsules containing said pharmaceutically active substance with a confectionery substance in a liquid phase to form a confectionery mixture, said confectionery substance containing water and being solidifiable into a solid matrix which can contain a small amount of water that has not solidified, and b) cooling the confectionery mixture to a temperature at which the confectionery substance solidifies with addition of a gas under pressure to form the confectionery formulation comprising the coated microcapsules surrounded by a confectionery matrix having a solid phase comprising the solid matrix, a possible liquid phase comprising the unsolidified water and a gas phase comprising the gas, said coated microcapsules comprising a water-proof coating to protect the pharmaceutically active substance from the unsolidified water.

2. A process as claimed in claim 1 wherein the confectionery matrix and the water-proof coating of the coated microcapsules are sufficiently soluble in a mouth of a patient to be treated so that the formulation can melt in the mouth without chewing.

3. A process as claimed in claim 2 wherein the confectionery matrix is ice cream and the water-proof coating has a melting point below about 30° C.

4. A process as claimed in claim 3 wherein the mixing in step a is done at a temperature of between about 0° C. and −1° C.

5. A process as claimed in claim 4 wherein the mixture is cooled to below about −18° C. in step b.

6. A process as claimed in claim 5 wherein the gas is an inert gas.

7. A process as claimed in claim 6 wherein the inert gas is nitrogen which is added in an amount sufficient to swell a volume of the confectionery mixture by about 50%–150%.

8. A process as claimed in claim 3 wherein the process comprises a step of coating the microcapsules with said water-proof coating immediately prior to the mixing in step a.

9. A process as claimed in claim 8 wherein the step of coating said microcapsules comprises spraying the microcapsules with a sufficient quantity of edible vegetal oil to coat the microcapsules, and blowing said sprayed microcapsules with air at a temperature sufficiently low to solidify the oil and to polish the microcapsules.

10. A process as claimed in claim 9 wherein, prior to coating the microcapsules with the water-proof coating, the process comprises polishing the microcapsules with a pharmacologically acceptable hydrophobic substance.

11. A process as claimed in claim 9 wherein the process comprises forming the formulation of step b into a candy and coating said candy with a layer of chocolate, caramel, water or a combination thereof.

12. A process as claimed in claim 11 wherein said candy is provided with score lines so that it can be readily subdivided.

13. A process as claimed in claim 11 wherein the process comprises hermetically sealing the candy in a thin-walled receptacle comprising a composite sheet with layers of paper, plastic, metal or a combination thereof.

14. A process as claimed in claim 5 wherein the process comprises storing the confectionery formulation at a temperature between about −20° C. and −40° C.

15. A confectionery formulation for the controlled release of a pharmaceutically active substance, said formulation comprising a) an edible binding matrix that is storable at a storage temperature of between about −18° C. and −40° C., said matrix comprising a solid phase, a liquid phase comprising eutectic water, and a gas phase at said storage temperature, said edible matrix being soluble in a mouth of a patient; and b) a plurality of microcapsules embedded in said matrix, each of said microcapsules comprising the pharmaceutically active substance and a coating comprising one or more hydrophobic substance or substances selected from the group consisting of a vegetal oil, a wax and a combination thereof, said hydrophobic substance or substances being present in said coating in an amount sufficient to protect said pharmaceutically active substance from said eutectic water during storage of the formulation at said storage temperature, said coating being soluble in the mouth of the patient.

16. A confectionery formulation as claimed in claim 15 wherein the binding matrix comprises ice cream.

17. A confectionery formulation as claimed in claim 15 wherein the binding matrix comprises ice lolly.

18. A confectionery formulation as claimed in claim 15 wherein the formulation comprises:

| | |
|---|---|
| Pharmaceutically active substance | 0.1–25% |
| Milk powder/FAO/WHO | 1–18% |
| Saccharose USP | 10–18% |
| Lecithin USP | 2–4% |
| Casein USP | 0.5–4% |
| Glucose USP | 2–4% |
| Vegetal gum USP | 0.1–1% |
| Synthetic sweetener USP | Desired Amount |
| Flavor USP | Desired Amount |
| Colorant USP | Desired Amount |
| Water USP sufficient quantity up to | 100% |

19. A confectionery formulation as claim 16 wherein the pharmaceutically active substance is a medicinal product selected from the group consisting of:

anti-inflammatory substances, factor for dilatation of the coronary artery, tranquilizers, nutritive additives, diuretics, medicines against migraine, anti-asthmatics, expectorants, antipyretics, anti-cholesterinemic agents, anti-lipidemic agents, anti-arrhythmics, ion-exchange resins, inorganic supplements, laxatives, vitamins, compounds binding the acids of the stomach, antitussives, anti-histaminics, alkaloids, and decongestives, said medicinal product being present in the formulation in an amount of about 0.1–25% by weight.

20. A process for rendering microcapsules comprising a pharmaceutically active substance suitable for inclusion in a confectionery matrix, said matrix being soluble in the mouth of a patient to be treated and being storable at a temperature at which the matrix comprises a solidified substance and eutectic water, said process comprising:

a) coating said microcapsules with a vegetal oil and mixing said coated microcapsules with said confectionery matrix at an initial temperature at which the matrix is in liquid phase whereby to form a mixture; and b) cooling the mixture to a solidifying temperature at which the matrix comprises the solidified substance and the eutectic water.

21. A process as claimed in claim 20 wherein the process comprises adding nitrogen gas under pressure to the mixture in step a.

22. A process as claimed in claim 20 wherein the confectionery matrix is ice cream, the initial temperature is about −18° C. to −1° C. and the solidifying temperature is about −18° C. or below.

* * * * *